US00PP21695P2

(12) United States Plant Patent
Oudshoorn

(10) Patent No.: US PP21,695 P2
(45) Date of Patent: Feb. 1, 2011

(54) ***SEDUM* PLANT NAMED 'CORAL REEF'**
(50) Latin Name: *Sedum telephium*
Varietal Denomination: Coral Reef

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/590,823

(22) Filed: Nov. 14, 2009

(51) Int. Cl.
*A01H 5/00* (2006.01)

(52) U.S. Cl. ..... Plt./479
(58) Field of Classification Search ..... Plt./479

See application file for complete search history.

*Primary Examiner*—Kent L Bell
(74) *Attorney, Agent, or Firm*—C. A. Whealy

(57) ABSTRACT

A new and distinct cultivar of *Sedum* plant named 'Coral Reef', characterized by its upright and compact plant habit; freely basally branching habit; dense and bushy growth habit; attractive white-colored flowers with greyed purple-colored centers; and good garden performance.

2 Drawing Sheets

Botanical designation: *Sedum telephium.*
Cultivar denomination: 'CORAL REEF'.

BACKGROUND OF THE INVENTION

The present invention relates to a new and distinct cultivar of *Sedum* plant, botanically known as *Sedum telephium* and hereinafter referred to by the name 'Coral Reef'.

The new *Sedum* plant is a product of a planned breeding program conducted by the Inventor in Rijpwetering, The Netherlands. The objective of the breeding program is to create new strong and healthy *Sedum* cultivars with numerous attractive flowers.

The new *Sedum* plant originated from a cross-pollination during the summer of 2005 in Rijpwetering, The Netherlands, of *Sedum telephium* 'Purple Emperor', not patented, as the female, or seed, parent with *Sedum telephium* 'Xenox', disclosed in U.S. Plant Pat. No. 16,888, as the male, or pollen, parent. The new *Sedum* plant was discovered and selected by the Inventor as a single flowering plant within the progeny of the stated cross-pollination in a controlled greenhouse environment in Rijpwetering, The Netherlands during the summer of 2006.

Asexual reproduction of the new *Sedum* plant by vegetative cuttings in a controlled environment in Rijpwetering, The Netherlands since the summer of 2008, has shown that the unique features of this new *Sedum* plant are stable and reproduced true to type in successive generations.

SUMMARY OF THE INVENTION

Plants of the new *Sedum* have not been observed under all possible environmental conditions. The phenotype may vary somewhat with variations in environment such as temperature and light intensity without, however, any variance in genotype.

The following traits have been repeatedly observed and are determined to be the unique characteristics of 'Coral Reef'. These characteristics in combination distinguish 'Coral Reef' as a new and distinct cultivar of *Sedum:*

1. Upright and compact plant habit.
2. Freely basally branching habit; dense and bushy growth habit.
3. Attractive white-colored flowers with greyed purple-colored centers.
4. Good garden performance.

Plants of the new *Sedum* differ from plants of the female parent, 'Purple Emperor', primarily in flower and leaf color as plants of 'Purple Emperor' have pink-colored flowers and greenish purple-colored leaves.

Plants of the new *Sedum* differ from plants of the male parent, 'Xenox', primarily in flower color as plants of 'Xenox' have orange white to greyed yellow-colored flowers.

Plants of the new *Sedum* can be compared to plants of *Sedum telephium* 'Postman's Pride', not patented. Plants of the new *Sedum* and 'Postman's Pride' differ in the following characteristics:

1. Plants of the new *Sedum* are more compact than plants of 'Postman's Pride'.
2. Plants of the new *Sedum* and 'Postman's Pride' differ in flower color as plants of 'Postman's Pride' have pinkish red purple-colored flowers.

BRIEF DESCRIPTION OF THE PHOTOGRAPHS

The accompanying colored photographs illustrate the overall appearance of the new *Sedum* plant, showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of typical flowering plants of 'Coral Reef' grown in an outdoor nursery.

The photograph at the top of the second sheet is a close-up view of typical inflorescences of 'Coral Reef'.

The photograph at the bottom of the second sheet is a close-up view of the upper (left) and lower (right) surfaces of typical leaves of 'Coral Reef'.

DETAILED BOTANICAL DESCRIPTION

The aforementioned photographs and following observations, measurements and values describe plants grown in Rijpwetering, The Netherlands, under commercial practice during the early autumn in an outdoor nursery with day temperatures ranging from 12° C. to 32° C. and night temperatures ranging from 6° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Sedum telephium* 'Coral Reef'.

Parentage:

*Female, or seed, parent.*—*Sedum telephium* 'Purple Emperor', not patented.

*Male, or pollen, parent.*—*Sedum telephium* 'Xenox', disclosed in U.S. Plant Pat. No. 16,888.

Propagation:

*Type.*—By vegetative cuttings.

*Time to initiate roots.*—About 10 to 15 days at 18° C.

*Time to produce a rooted young plant.*—About three months at 16° C. to 22° C.

*Root description.*—Moderately thick and moderately fleshy; pinkish white to medium brown in color.

*Rooting habit.*—Moderately freely branching; moderately sparse.

Plant description:

*Plant form/habit.*—Herbaceous perennial; upright and compact plant habit; inverted triangle; moderately vigorous growth habit; freely basally branching habit with about 14 branches developing per plant; dense and bushy growth habit.

*Plant height.*—About 41.3 cm.

*Plant width* (*spread*).—About 26.1 cm.

*Lateral branches.*—Length: About 12.9 cm. Diameter: About 3.5 mm. Internode length: About 5.2 cm. Strength: Strong. Texture: Smooth, glabrous. Color: Between 176B and 182B to 182C.

Foliage description:

*Arrangement.*—Opposite, simple; sessile.

*Length.*—About 7.1 cm.

*Width.*—About 3.6 cm.

*Shape.*—Ovate.

*Apex.*—Bluntly acute.

*Base.*—Cordate.

*Margin.*—Irregularly and shallowly dentate.

*Texture, upper and lower surfaces.*—Smooth, glabrous; succulent.

*Venation pattern.*—Pinnate.

*Color.*—Developing leaves, upper surface: Close to 147A. Developing leaves, lower surface: Close to 189A. Fully expanded leaves, upper surface: Between N186A and 203A; venation, close to 187A. Fully expanded leaves, lower surface: Between 147A and 189A; venation, close to 146A to 146B; venation towards the base, tinged with close to 176B.

Flower description:

*Flower type/habit.*—Small rotate flowers arranged in terminal compound cymes; flowers face upright to slightly outward; freely flowering habit with about 120 flowers per inflorescence.

*Fragrance.*—None detected.

*Natural flowering season.*—Continuously flowering during August and September in The Netherlands.

*Postproduction longevity.*—Flowers last about two weeks on the plant; flowers persistent.

*Flower buds.*—Height: About 5 mm. Diameter: About 2.5 mm. Shape: Ovate. Color: Close to 182D; towards the apex, close to 182B.

*Inflorescence height.*—About 6.6 cm.

*Inflorescence diameter.*—About 7 cm.

*Flower diameter.*—About 9 mm.

*Flower depth.*—About 6 mm.

*Petals.*—Quantity per flower: Typically five in a single whorl; petals fused towards the base. Length: About 5 mm. Lobe width: About 2 mm. Shape: Ovate. Apex: Acute. Margin: Entire. Texture, upper and lower surfaces: Smooth, glabrous. Color: When opening and fully opened, upper surface: Close to N155D; towards the base, close to 184B to 184C; color becoming closer to 186D to lighter than 186D with development. When opening and fully opened, lower surface: Close to 186C to 186D; towards the base, close to 186A.

*Sepals.*—Quantity per flower: Typically five in a single whorl, fused at the base. Length: About 1.5 mm. Width: About 1 mm. Shape: Narrowly ovate. Apex: Acute. Margin: Entire. Texture, upper and lower surfaces: Smooth, glabrous. Color: When opening, upper surface: Close to 148C. When opening, lower surface: Close to 148A to 148B tinged with close to 186D. Fully opened, upper surface: Close to 148C. Fully opened, lower surface: Between 148A and 183D.

*Peduncles.*—Length: About 5.1 cm. Diameter: About 2 mm. Angle: Erect to about 30° from vertical. Strength: Moderately strong. Texture: Smooth, glabrous. Color: Between 176B and 182B to 182C.

*Pedicels.*—Length: About 4 mm. Diameter: About 0.6 mm. Angle: Erect to about 50° from vertical. Strength: Moderately strong. Texture: Smooth, glabrous. Color: Between 176B and 182B to 182C.

*Reproductive organs.*—Stamens: Quantity per flower: Typically ten. Filament length: About 4 mm. Filament color: Close to N155D. Anther shape: Broadly oblong, flattened. Anther length: About 0.5 mm. Anther color: Close to 172B. Pollen amount: Scarce. Pollen color: Close to 5B to 5C. Pistils: Quantity per flower: Five. Pistil length: About 4 mm. Stigma shape: Pointed. Stigma color: Between N155B and 186D. Style length: About 4 mm. Style color: Close to 186A and 186B. Ovary color: Close to 186B.

*Seed/fruit.*—Seed and fruit development have not been observed.

Disease/pest resistance: Plants of the new *Sedum* have not been observed to be resistant to pathogens and pests common to *Sedum*.

Garden performance: Plants of the new *Sedum* have been observed to have good garden performance and to tolerate rain and wind. Plants of the new *Sedum* tolerate high temperatures of about 35° C. and are winter hardy to USDA Hardiness Zone 5.

It is claimed:

1. A new and distinct *Sedum* plant named 'Coral Reef' as illustrated and described.

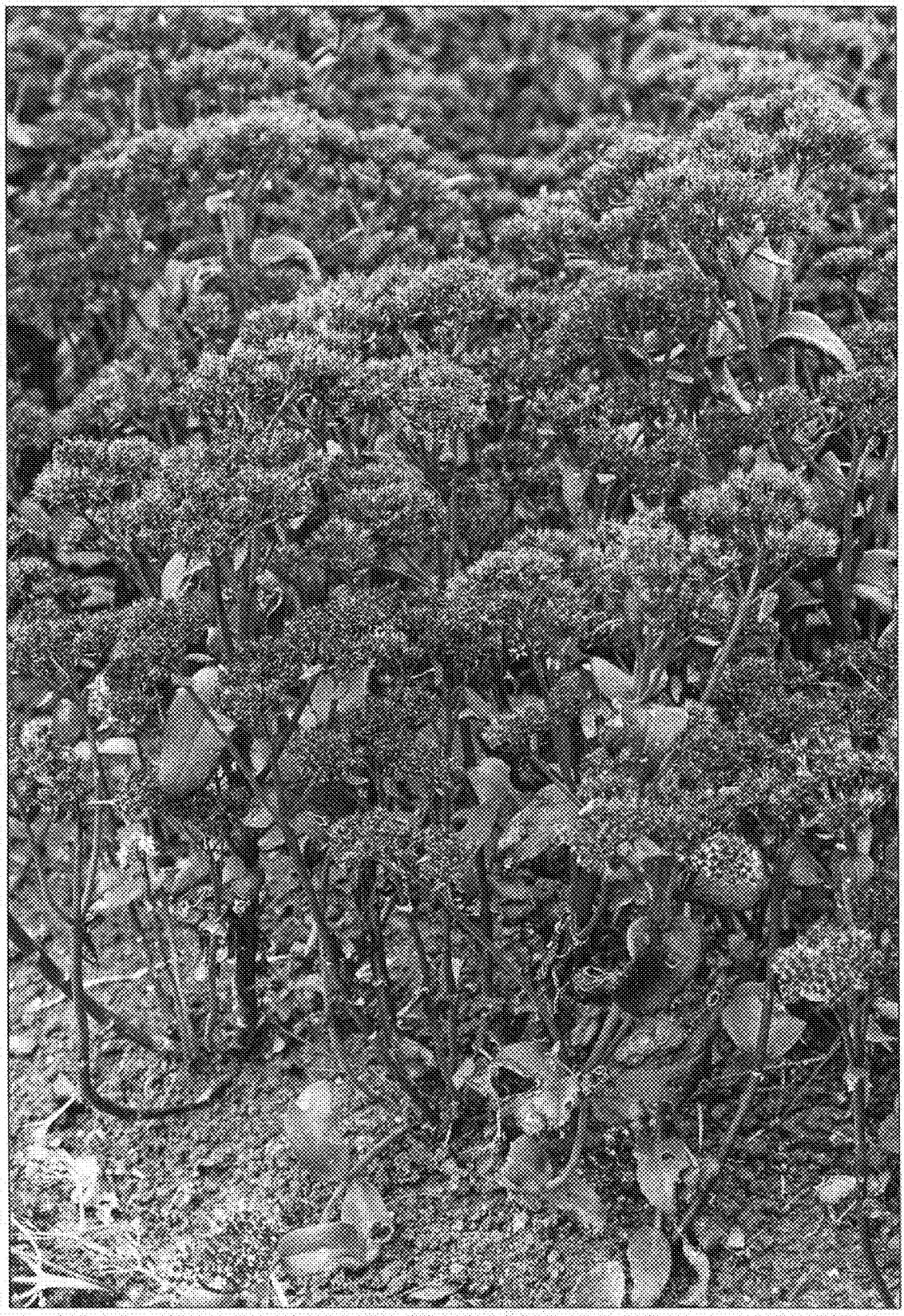

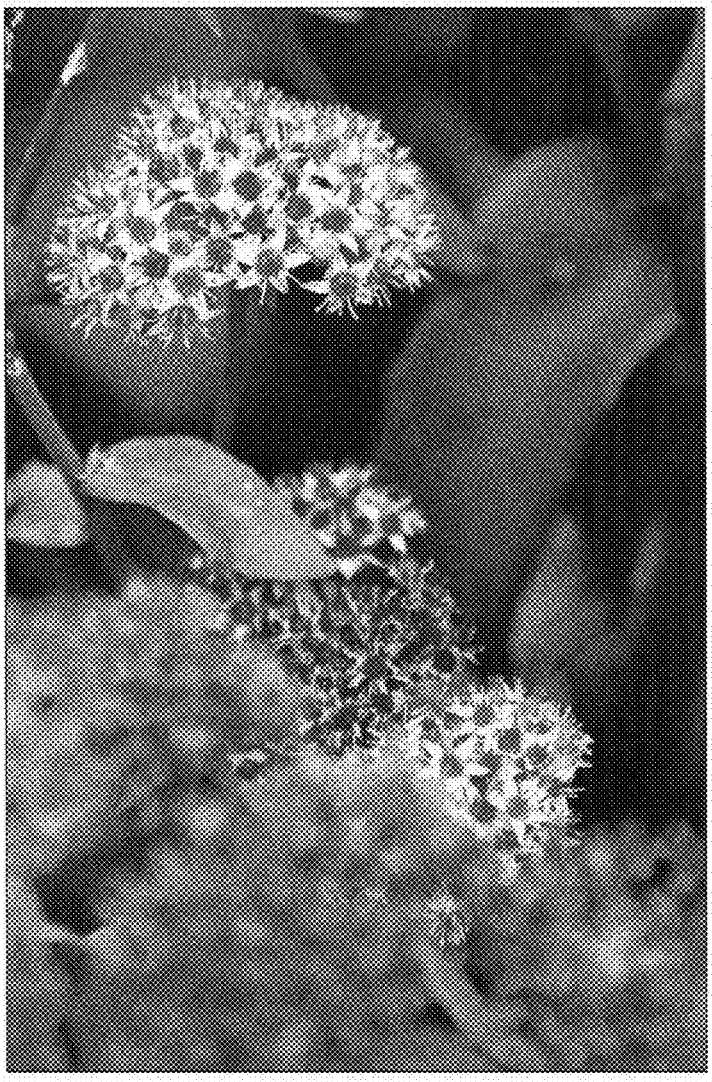
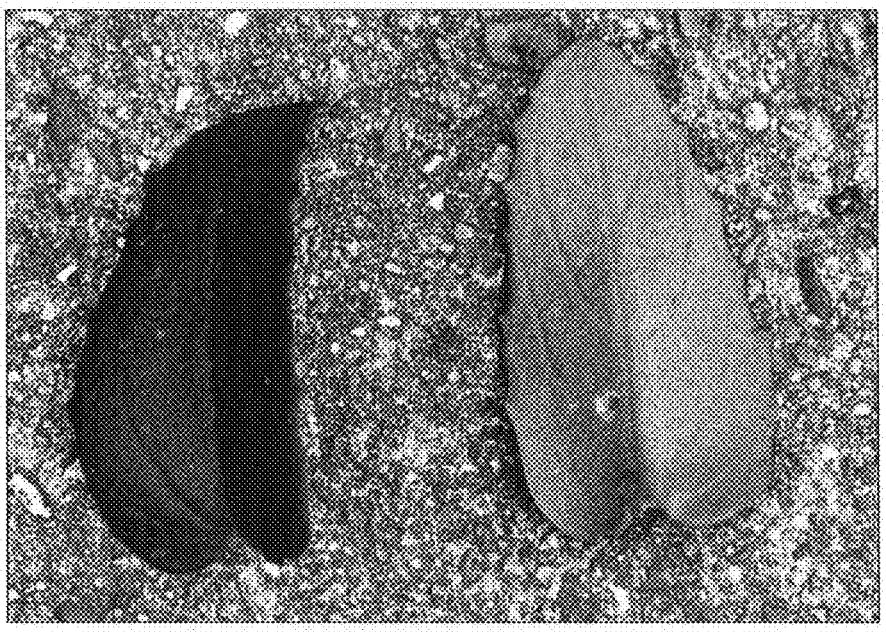

* * * * *